US00PP29910P2

(12) United States Plant Patent
Trees

(10) Patent No.: US PP29,910 P2
(45) Date of Patent: Nov. 27, 2018

(54) ***PHLOX* PLANT NAMED 'CHERRY CREAM'**

(50) Latin Name: *Phlox paniculata*
Varietal Denomination: Cherry Cream

(71) Applicant: Ball Horticultural Company, West Chicago, IL (US)

(72) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/731,884

(22) Filed: Aug. 18, 2017

(51) Int. Cl.
*A01H 5/02* (2018.01)

(52) U.S. Cl.
USPC ..... Plt./320

(58) Field of Classification Search
USPC ..... Plt./320
See application file for complete search history.

*Primary Examiner* — Keith O. Robinson
(74) *Attorney, Agent, or Firm* — Audrey Charles

(57) ABSTRACT

A new and distinct cultivar of *Phlox* plant named 'Cherry Cream', characterized by its dark reddish purple and white bicolored flowers, medium green-colored foliage, and moderately vigorous, upright growth habit, is disclosed.

1 Drawing Sheet

Latin name of genus and species of plant claimed: *Phlox paniculata.*

Variety denomination: 'Cherry Cream'.

BACKGROUND OF THE INVENTION

The present invention relates to a new and distinct cultivar of *Phlox* plant botanically known as *Phlox paniculata* and hereinafter referred to by the cultivar name 'Cherry Cream'.

The new cultivar originated in a controlled breeding program in Guadalupe, Calif. during October 2011. The objective of the breeding program was the development of *Phlox* cultivars with increased powdery mildew resistance and a compact growth habit.

The new *Phlox* cultivar is the result of open-pollination. The female (seed) parent of the new cultivar is 'Laura', not patented, characterized by its deep fuchsia-purple and white bicolored flowers, dark green-colored foliage, and vigorous, upright growth habit. The male (pollen) parent of the new cultivar is unknown. The new cultivar was discovered and selected as a single flowering plant within the progeny of the above stated open-pollination during July 2012 in a controlled environment in Guadalupe, Calif.

Asexual reproduction of the new cultivar by terminal stem cuttings since July 2012 in Guadalupe, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Cherry Cream' as a new and distinct cultivar of *Phlox* plant:

1. Dark reddish-purple and white bicolored flowers;
2. Medium green-colored foliage; and
3. Moderately vigorous, upright growth habit.

Plants of the new cultivar differ from plants of the female parent primarily in flower color and reduced growth vigor.

Of the many commercially available *Phlox* cultivars, the most similar in comparison to the new cultivar is Flame White Eye 'Barsixty', U.S. Plant Pat. No. 22,211. However, in side by side comparisons, plants of the new cultivar differ from plants of 'Barsixty' in at least the following characteristics:

1. Plants of the new cultivar have a flower color different from plants of 'Barsixty';
2. Plants of the new cultivar have smaller diameter flowers than plants of 'Barsixty'; and
3. Plants of the new cultivar have lower growth vigor than plants of 'Barsixty'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Cherry Cream'. The plants were approximately six months old. Plants were grown in one-gallon containers for approximately five weeks in a greenhouse and 14 weeks outdoors in Elburn, Ill. Plants were given two pinches, one before transplant and one at transplant.

DETAILED BOTANICAL DESCRIPTION

Figure 1:
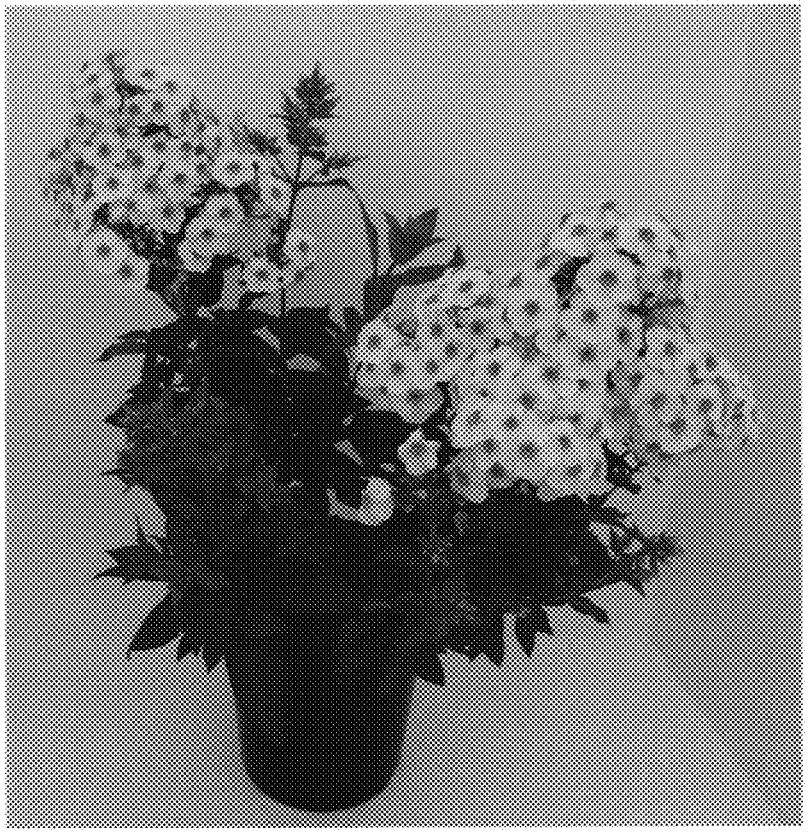
FIG. 1 illustrates a side view of the overall growth and flowering habit of 'Cherry Cream'.
Figure 2:
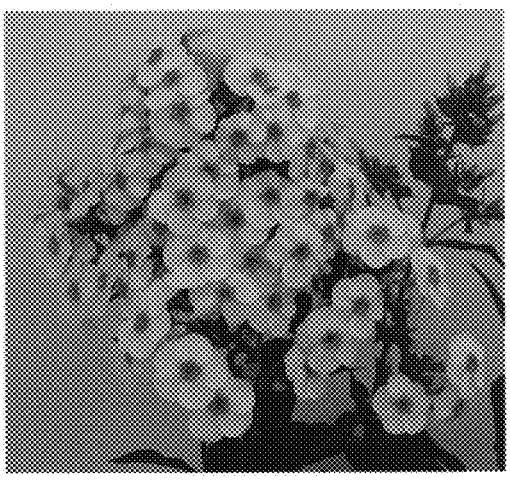
FIG. 2 illustrates a close-up view of an individual inflorescence of 'Cherry Cream'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2017 under natural light conditions in West Chicago, Ill.

The following descriptions and measurements describe approximately six-month old plants produced from cuttings from stock plants and grown under conditions comparable to those used in commercial practice. The plants were grown in one-gallon containers for approximately five weeks in a greenhouse and 14 weeks outdoors in Elburn, Ill. Plants were given two pinches, one before transplant and one at transplant. Greenhouse temperatures were maintained at approximately 60° F. to 68° F. (15.5° C. to 20° C.) during the day and approximately 55° F. to 60° F. (13° C. to 15.5° C.) during the night. No supplemental lighting was provided. Measurements and numerical values represent averages of typical plants.

Botanical classification: *Phlox paniculata* 'Cherry Cream'.

Parentage:

*Female parent*.—'Laura', not patented.

*Male parent*.—Unknown.

Propagation:

*Type cutting*.—Terminal stem.

*Time to initiate roots*.—Approximately 10 to 12 days.

*Time to produce a rooted cutting*.—Approximately 42 to 49 days.

*Root description*.—Fine to medium thickness, medium density.

*Rooting habit*.—Freely branching, medium density.

Plant description:

*Commercial crop time*.—Approximately 10 to 12 weeks from a rooted cutting to finish in a 15 cm pot.

*Growth habit and general appearance*.—Herbaceous perennial, moderately vigorous, upright growth habit.

*Hardiness*.—USDA Zone 4a (−30° F. to −25° F./−34.4° C. to −31.7° C.).

*Size*.—Height: Approximately 42.0 cm. Width: Approximately 36.0 cm.

*Branching habit*.—Low to moderate basal branching. Pinching will improve branching.

*Branch*.—Quantity: Approximately 3 basal branches. Shape: Round. Strength: Moderate, slightly brittle. Length to base of inflorescence: Approximately 29.0 cm. Diameter: Approximately 3.0 mm to 5.0 mm. Length of central internode: Approximately 2.2 cm. Texture: Glabrous. Color of young stems: 146C. Color of mature stems: 146C, becoming woody 199C with age.

Foliage description:

*General description*.—Quantity of leaves per main branch: Approximately 10. Fragrance: Moderately fragrant; sweet, pleasant. Form: Simple. Arrangement: Opposite.

*Leaves*.—Shape: Elliptic, slightly carinate. Margin: Entire, minutely ciliate. Apex: Acute. Base: Rounded. Venation pattern: Pinnate. Length: Approximately 9.0 cm. Width: Approximately 3.5 cm. Texture of upper surface: Sparsely pubescent. Texture of lower surface: Densely pubescent. Color of upper surface of young and mature foliage: 137A with venation of 145C. Color of lower surface of young and mature foliage: 147C with venation of 145D.

*Petioles*.—Length: Approximately 2.0 mm. Width: Approximately 2.0 mm. Texture: Glabrous. Color: 145D.

Flowering description:

*Flowering habit*.—'Cherry Cream' is freely flowering under outdoor growing conditions with substantially continuous blooming from late spring throughout summer.

*Lastingness of individual flower on the plant*.—Approximately 10 days.

Inflorescence description:

*General description*.—Type: Compound terminal panicle, flowers face upright and outwardly, self-cleaning. Quantity per plant: Approximately 7. Fragrance: Moderately sweet and pleasant. Height of primary: Approximately 22.0 cm. Width of primary: Approximately 19.0 cm. Quantity of fully open flowers per primary inflorescence: Approximately 150. Height of secondary: Approximately 8.5 cm. Width of secondary: Approximately 8.0 cm. Quantity of fully open flowers per secondary inflorescence: Approximately 30.

*Peduncle*.—Strength: Strong. Aspect: Primary erect, axillary acute angle to stem. Length of primary: Approximately 11.5 cm. Diameter of primary: Approximately 5.0 mm. Length of axillary: Approximately 2.0 cm to 7.0 cm. Diameter of axillary: Approximately 2.0 mm. Texture: Moderately pubescent. Color: 146C.

Flower description:

*Type*.—Single.

*Bud*.—Rate of opening: Generally takes 3 to 4 days for bud to progress from first color to fully open flower.

*Bud just before opening*.—Shape: Oblanceolate. Length: Approximately 1.9 cm. Diameter: Approximately 4.0 mm. Color: NN155A with N74C.

*Corolla*.—Shape: Salverform. Diameter: Approximately 2.7 cm. Depth: Approximately 2.2 cm.

*Petals*.—Quantity: Typically 5 in a single whorl, base fused into a narrow tube. Lobe shape: Obovate. Margin: Entire. Apex: Obtuse. Lobe length: Approximately 1.2 cm. Lobe width: Approximately 1.3 cm. Texture of upper and lower surfaces: Smooth, glabrous. Color of upper surface when first and fully open: NN155D with base of N74A. Color of lower surface when first and fully open: NN155D with a faint overlay of N74B at base.

*Corolla tube*.—Length: Approximately 2.0 cm. Diameter at distal end: Approximately 3.0 mm. Diameter at proximal end: Approximately 2.0 mm. Texture of outer surface: Sparsely pubescent. Texture of inner surface: Smooth, glabrous with lower 5.0 mm densely pubescent. Color of inner surface: N74D with NN155D at base. Color of outer surface: N74C with NN155D at base.

*Calyx*.—Shape: Cupped. Length: Approximately 8.0 mm. Diameter: Approximately 3.0 mm.

*Sepals*.—Quantity per flower: 5, lower half fused. Shape: Lanceolate. Apex: Narrowly apiculate. Length: Approximately 8.0 mm. Width: Approximately 2.0 mm. Texture of outer surface: Sparsely pubescent. Texture of inner surface: Smooth, glabrous. Color of inner surface: 146C with tip of and central streak on upper half of N186A. Color of outer surface: 146D with tip of and central streak on upper half of N186A.

*Pedicel*.—Strength: Strong, flexible. Aspect: Primary erect, axillary acute angle to peduncle. Length: Approximately 3.0 mm. Diameter: Approximately 1.0 mm. Texture: Densely pubescent. Color: 146C.

*Reproductive organs*.—Androecium: Stamen quantity: 5 per flower, adnate to corolla tube. Stamen length: Approximately 2.1 cm. Filament length of free portion: Approximately 0.5 mm. Anther shape: Oblong, basifixed. Anther length: Approximately 2.0 mm. Anther color: 158B. Pollen amount: Abundant. Pollen color: 155D. Gynoecium: Pistil quantity: 1 per flower. Pistil length: Approximately 2.1 cm. Stigma shape: Cleft, three-parted. Stigma color: 145D. Style length: Approximately 1.9 cm. Style color: 145D. Ovary length: Approximately 2.0 mm. Ovary color: 144A.

Seed and fruit production: Neither seed nor fruit production has been observed.

Disease and pest resistance: Resistance to pathogens and pests common to *Phlox* has not been observed.

What is claimed is:

1. A new and distinct cultivar of *Phlox* plant named 'Cherry Cream', substantially as herein illustrated and described.

* * * * *